United States Patent
Sim

(10) Patent No.: US 11,787,408 B2
(45) Date of Patent: Oct. 17, 2023

(54) SYSTEM AND METHOD FOR CONTROLLING VEHICLE BASED ON CONDITION OF DRIVER

(71) Applicant: MANDO CORPORATION, Pyeongtaek-si (KR)

(72) Inventor: Sang Kyun Sim, Anyang-si (KR)

(73) Assignee: HL Klemove Corp., Incheon (KR)

( * ) Notice: Subject to any disclaimer, the term of this patent is extended or adjusted under 35 U.S.C. 154(b) by 11 days.

(21) Appl. No.: 16/180,468

(22) Filed: Nov. 5, 2018

(65) Prior Publication Data
US 2019/0135291 A1    May 9, 2019

(30) Foreign Application Priority Data
Nov. 3, 2017    (KR) .................. 10-2017-0146215

(51) Int. Cl.
*B60W 30/18* (2012.01)
*B60W 40/08* (2012.01)
(Continued)

(52) U.S. Cl.
CPC ..... *B60W 30/18163* (2013.01); *A61B 5/0077* (2013.01); *A61B 5/1112* (2013.01);
(Continued)

(58) Field of Classification Search
CPC ..... B60W 30/10–12; B60W 30/18163; B60W 2040/0818–0863; B60W 2540/26;
(Continued)

(56) References Cited

U.S. PATENT DOCUMENTS 8,618,922 B2 * 12/2013 Debouk .............. B60W 50/038
340/439
2003/0229447 A1 * 12/2003 Wheatley ............. B62D 15/029
701/300
(Continued)

FOREIGN PATENT DOCUMENTS

DE         198 03 158 C1    5/1999
DE    10 2011 086 241 A1    5/2013
(Continued)

OTHER PUBLICATIONS

Takeda—English description and claims of JP-2007331652-A via Espacenet patent translate, retrieved Jun. 4, 2020 (Year: 2020).*
(Continued)

*Primary Examiner* — Jeffrey C Boomer
*Assistant Examiner* — Paul Allen
(74) *Attorney, Agent, or Firm* — Morgan, Lewis & Bockius LLP

(57) ABSTRACT

A system and method for controlling a vehicle based on a driver status are disclosed. The vehicle control system includes various sensing devices (including a camera, a vehicle dynamics sensor, a vehicle around view monitoring (AVM) camera, a periphery surveillance sensor, and a navigation device) and an electronic control unit (ECU). The ECU may analyze a driver status through the driver's face and pupils recognized by output signals of the sensing devices. If the driver has no intention to drive the vehicle, the ECU may control the vehicle to stop on a road shoulder, resulting in guarantee of safer driving.

11 Claims, 5 Drawing Sheets

(51) Int. Cl.

| | | |
|---|---|---|
| B60Q 1/52 | (2006.01) | |
| G06T 7/73 | (2017.01) | |
| B60W 30/14 | (2006.01) | |
| A61B 5/18 | (2006.01) | |
| A61B 5/16 | (2006.01) | |
| B60W 50/10 | (2012.01) | |
| B60K 28/06 | (2006.01) | |
| A61B 5/00 | (2006.01) | |
| B60W 30/10 | (2006.01) | |
| B60W 30/182 | (2020.01) | |
| A61B 5/11 | (2006.01) | |
| G06V 20/56 | (2022.01) | |
| G06V 20/59 | (2022.01) | |
| G06V 40/16 | (2022.01) | |
| G06V 40/18 | (2022.01) | |
| B60W 10/188 | (2012.01) | |
| B60W 10/20 | (2006.01) | |
| G05D 1/00 | (2006.01) | |
| B60W 50/14 | (2020.01) | |

(52) U.S. Cl.
CPC ............ *A61B 5/163* (2017.08); *A61B 5/165* (2013.01); *A61B 5/18* (2013.01); *A61B 5/4809* (2013.01); *A61B 5/6893* (2013.01); *B60K 28/06* (2013.01); *B60Q 1/52* (2013.01); *B60W 10/188* (2013.01); *B60W 10/20* (2013.01); *B60W 30/10* (2013.01); *B60W 30/143* (2013.01); *B60W 30/182* (2013.01); *B60W 40/08* (2013.01); *B60W 50/10* (2013.01); *B60W 50/14* (2013.01); *G05D 1/0055* (2013.01); *G05D 1/0088* (2013.01); *G06T 7/73* (2017.01); *G06V 20/588* (2022.01); *G06V 20/597* (2022.01); *G06V 40/166* (2022.01); *G06V 40/193* (2022.01); *A61B 5/1122* (2013.01); *A61B 2560/0242* (2013.01); *A61B 2562/04* (2013.01); *B60W 2040/0818* (2013.01); *B60W 2420/42* (2013.01); *B60W 2540/26* (2013.01); *B60W 2554/4041* (2020.02); *B60W 2900/00* (2013.01); *G05D 2201/0213* (2013.01); *G06T 2207/30201* (2013.01)

(58) Field of Classification Search
CPC ..... B60W 2540/225; B60K 28/06–066; A61B 5/163; A61B 5/18; A61B 5/6893; A61B 5/165; A61B 5/00; G05D 1/00; B62D 15/00
See application file for complete search history.

(56) References Cited

U.S. PATENT DOCUMENTS

| | | | | |
|---|---|---|---|---|
| 2006/0072792 | A1* | 4/2006 | Toda ............... | B60R 25/305 382/115 |
| 2011/0178680 | A1* | 7/2011 | Kato ............... | B60T 7/14 701/41 |
| 2011/0241862 | A1* | 10/2011 | Debouk ............ | B60W 50/035 340/439 |
| 2013/0054090 | A1* | 2/2013 | Shin ............... | B60K 28/06 701/36 |
| 2014/0111369 | A1* | 4/2014 | Oh ................. | B60Q 9/006 342/52 |
| 2015/0158427 | A1* | 6/2015 | Lee ................ | B60Q 9/008 701/1 |
| 2016/0001781 | A1* | 1/2016 | Fung .............. | G16H 50/20 701/36 |
| 2016/0167661 | A1* | 6/2016 | Kuehne ........... | B60W 30/18163 701/36 |
| 2016/0170413 | A1* | 6/2016 | Mueller .......... | G01C 21/00 701/23 |
| 2017/0057510 | A1* | 3/2017 | Herbach .......... | B62D 15/0265 |
| 2017/0060234 | A1* | 3/2017 | Sung ............... | G06F 3/1431 |
| 2017/0088165 | A1* | 3/2017 | Raphael .......... | B62D 6/001 |
| 2017/0158054 | A1* | 6/2017 | Munaoka ......... | B60R 22/48 |
| 2017/0285741 | A1* | 10/2017 | Park ............... | G06K 9/00617 |
| 2018/0029604 | A1* | 2/2018 | Niino .............. | B60W 10/20 |
| 2018/0065625 | A1* | 3/2018 | Tijerina .......... | B60W 30/06 |
| 2018/0093675 | A1* | 4/2018 | Holub ............. | B60W 30/14 |
| 2018/0120837 | A1* | 5/2018 | Regmi ............ | A61B 5/01 |
| 2018/0208209 | A1* | 7/2018 | Al-Dahle ........ | B60W 10/22 |
| 2018/0224851 | A1* | 8/2018 | Park ............... | G05D 1/027 |
| 2018/0267557 | A1* | 9/2018 | Yan ................ | B60W 50/0098 |
| 2019/0056732 | A1* | 2/2019 | Aoi ................ | B60W 50/082 |
| 2019/0126821 | A1* | 5/2019 | Ho ................. | G06K 9/00818 |
| 2019/0126927 | A1* | 5/2019 | Uejima ........... | B60K 28/06 |
| 2020/0039508 | A1* | 2/2020 | Onishi ............ | B60W 50/14 |
| 2021/0282639 | A1* | 9/2021 | Yokoyama ...... | G02B 27/02 |

FOREIGN PATENT DOCUMENTS

| | | | |
|---|---|---|---|
| DE | 10 2015 220 356 A1 | | 4/2017 |
| EP | 2 657 921 A1 | | 10/2013 |
| JP | 2000351337 A | * | 12/2000 |
| JP | 2007331652 A | * | 12/2007 |
| JP | 2009151522 A | * | 7/2009 |
| JP | 2009-280015 A | | 12/2009 |
| JP | 4740399 B2 | | 8/2011 |
| JP | 2015-210734 A | | 11/2015 |
| JP | 2017-049636 A | | 3/2017 |
| KR | 10-2013-0023535 A | | 3/2013 |
| KR | 10-2014-0050424 A | | 4/2014 |
| KR | 10-1470190 B1 | | 12/2014 |
| KR | 2016-0024994 A | | 3/2016 |
| KR | 2017-0064910 A | | 6/2017 |

OTHER PUBLICATIONS

Niibe, Tadayuki—English Description of JP-2000351337-A via Espacenet Patent Translate, retrieved Nov. 16, 2020 (Year: 2020).*
Nanami, Takeshi—English description of JP-2009151522-A via Espacenet Patent Translate, retrieved Nov. 8, 2021. (Year: 2021).*
Partial Search Report with Provisional Opinion issued in corresponding European Application No. 18204080.8, dated Apr. 25, 2019.

* cited by examiner

[FIG. 1]
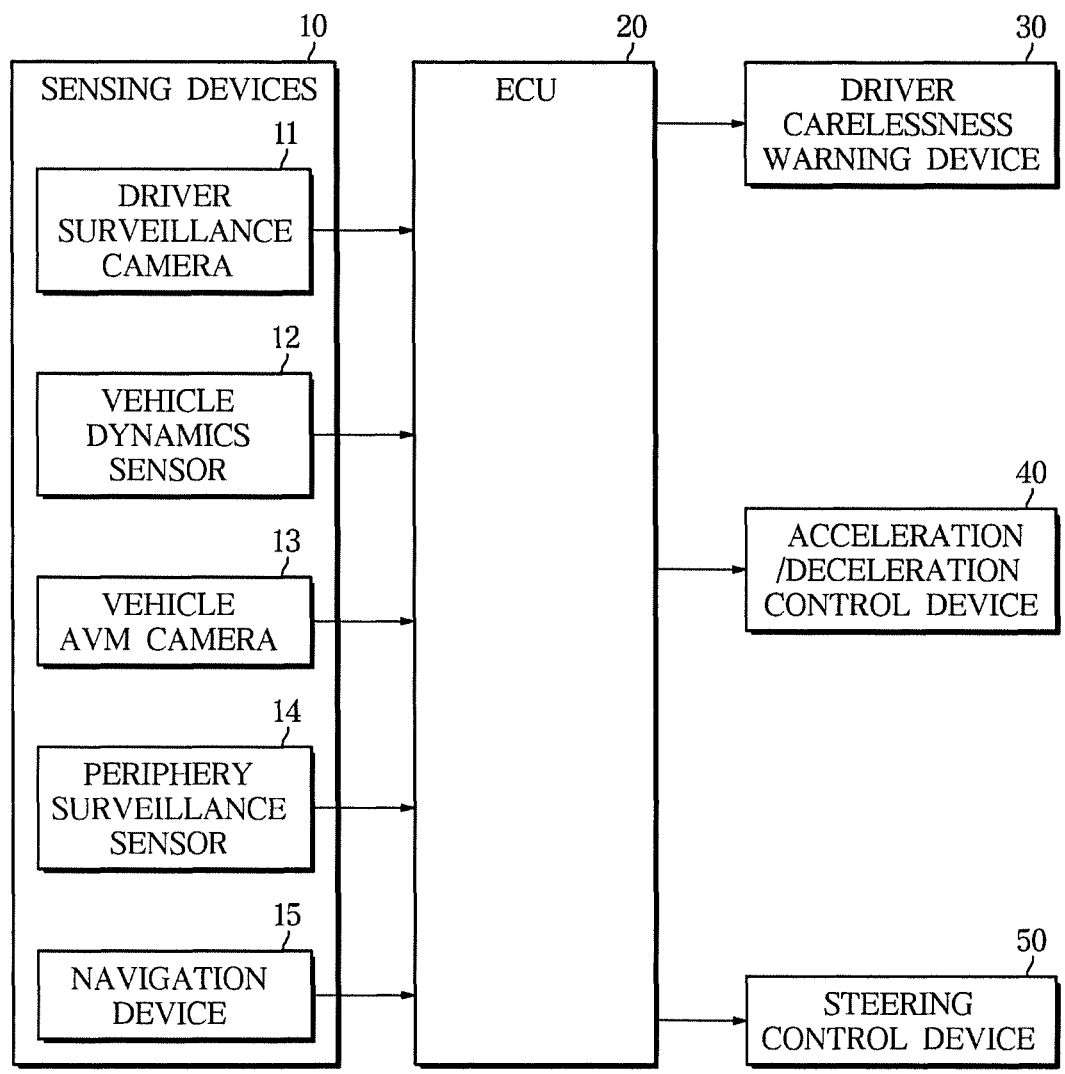

[FIG. 2]
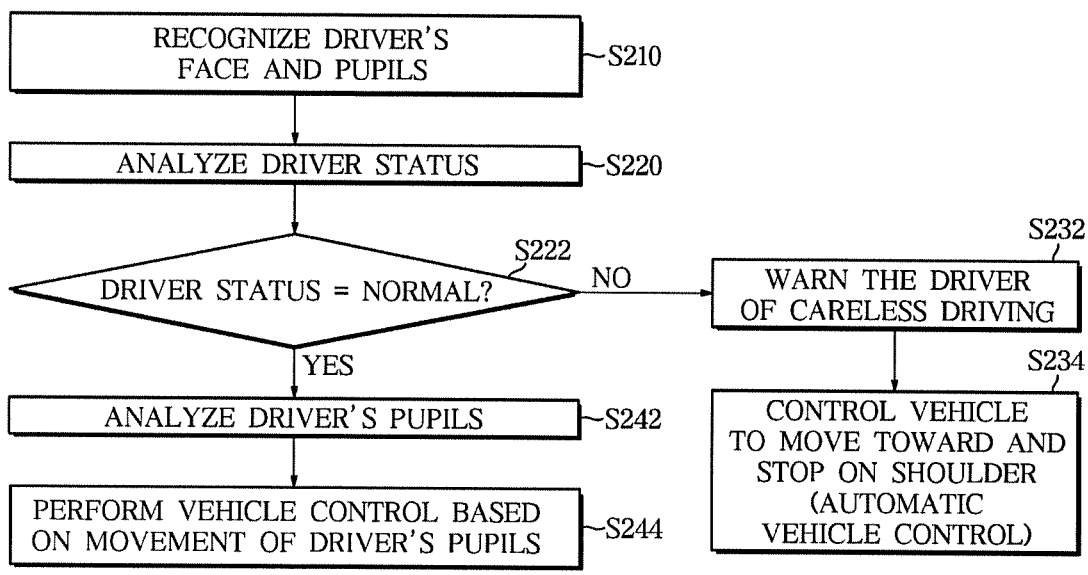

[FIG. 3]
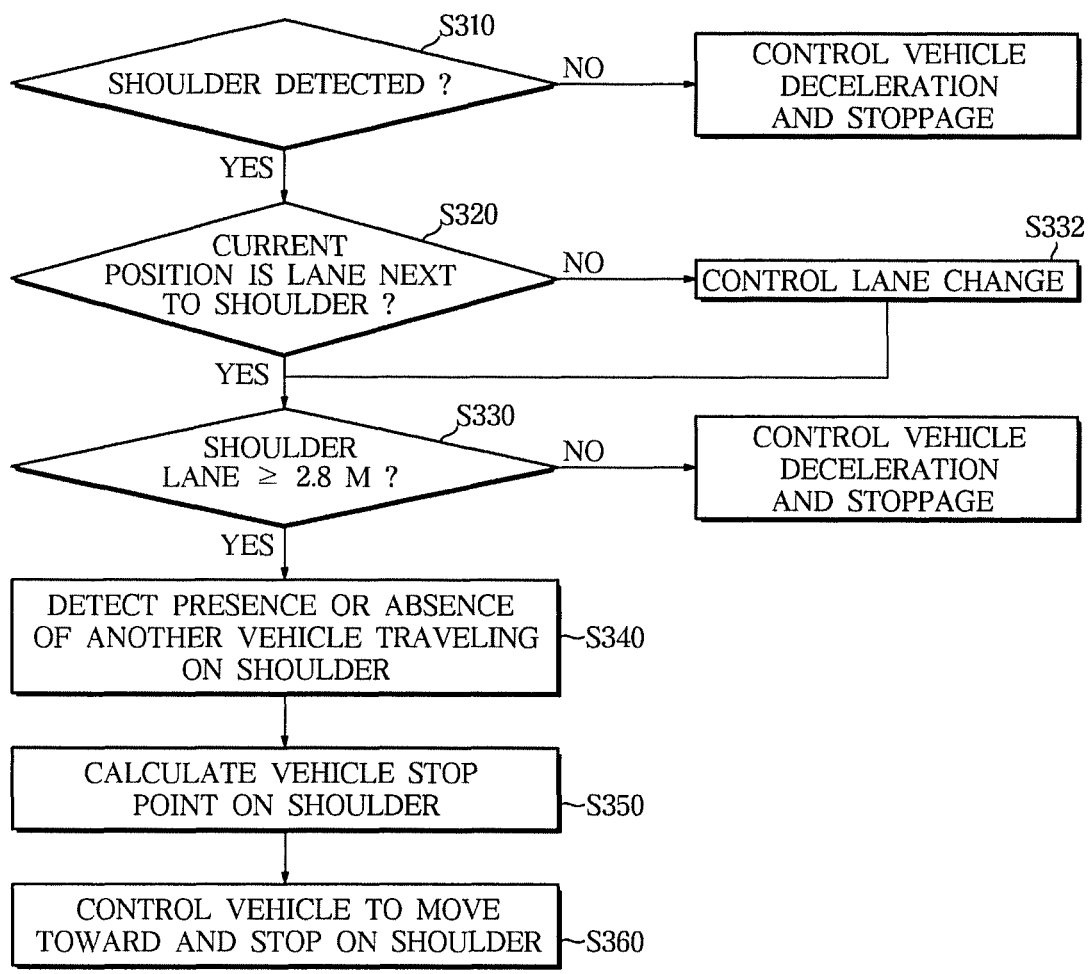

[FIG. 4]
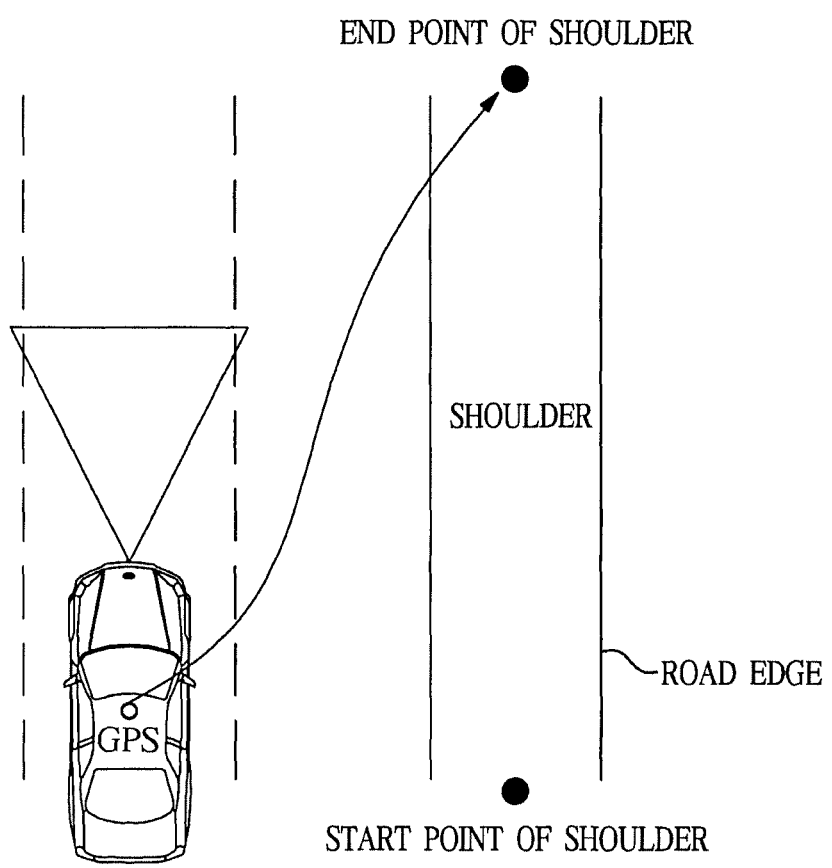

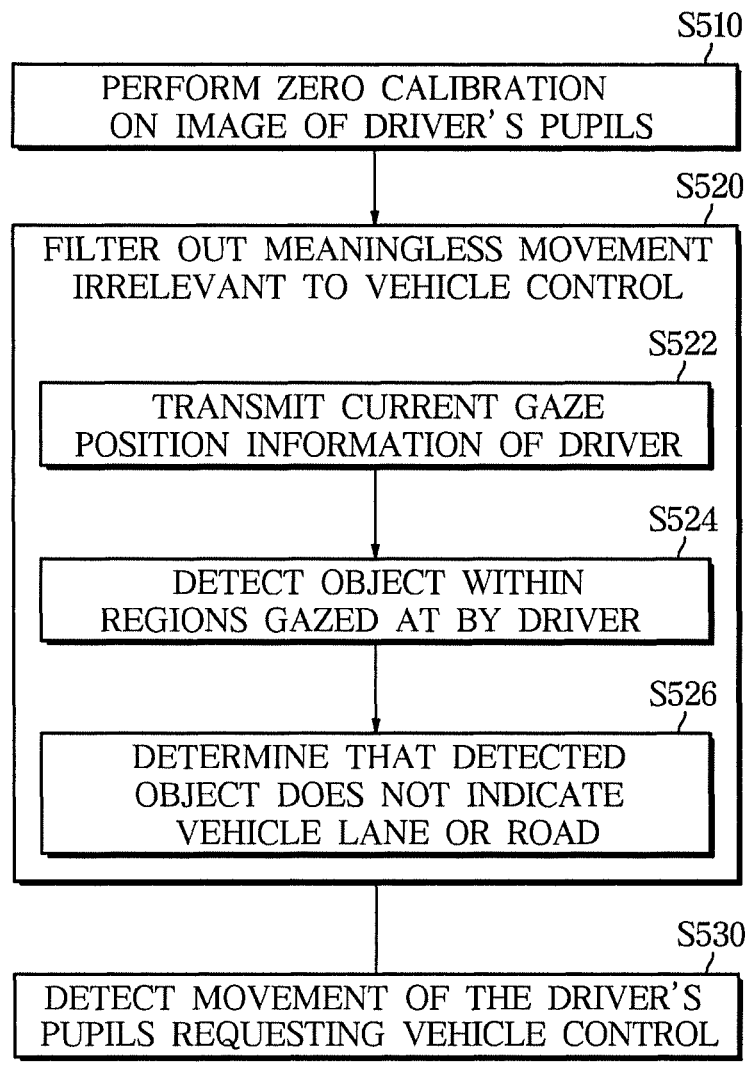
[FIG. 5]

SYSTEM AND METHOD FOR CONTROLLING VEHICLE BASED ON CONDITION OF DRIVER

CROSS-REFERENCE TO RELATED APPLICATION

This application is based on and claims priority under 35 U.S.C. § 119 to Korean Patent Application No. 10-2017-0146215, filed on Nov. 3, 2017 in the Korean Intellectual Property Office, the disclosure of which is incorporated by reference in its entirety.

BACKGROUND

1. Field

Embodiments of the present disclosure relate to a system and method for controlling a vehicle based on a driver status, and more particularly to a system and method for controlling a vehicle based on a driver status, which analyze a driver status by monitoring the driver's face and pupils during vehicle driving, and control the vehicle to stop on a road shoulder when it seems that the driver has no intention to drive the vehicle, resulting in safer and more stable vehicle driving.

2. Description of the Related Art

Generally, an Advanced Driver Assistance System (ADAS) may autonomously recognize some of many situations capable of occurring during vehicle driving, and may determine what situations have occurred, such that the ADAS can autonomously control mechanical devices based on the determined situations. The ADAS has been designed to assist or help a vehicle driver in a complicated vehicle control process, and has been intensively researched and developed to complete autonomous driving technology.

A representative example of the ADAS embedded in the vehicle may include an Autonomous Emergency Brake (AEB) system, a Lane Keeping Assist System (LKAS), an Advanced Smart Cruise Control (ASCC) system, an Active Blind Spot Detection (ABSD) system, an Around View Monitoring (AVM) system, etc. The AEB system may control the vehicle to autonomously decelerate or stop although the driver does not depress a brake pedal in a dangerous situation having a higher possibility of collision with peripheral objects. The LKAS determines whether a vehicle deviates from a current lane or is scheduled to deviate from the current lane. If the vehicle has deviated from the current lane or is scheduled to deviate from the current lane, the LKAS performs lane keeping control in a manner that the vehicle can maintain the current lane, or performs lane departure warning to inform the driver of a lane departure state or a lane departure expectation state. The ASCC system may control the vehicle to travel on a road at a predefined speed, while simultaneously maintaining a constant distance to a vehicle ahead. The ABSD system may determine whether there is a high possibility of collision in a blind spot, such that the ABSD system may guide a host vehicle to safely perform lane change when high possibility of collision is decided. The AVM system may visually display peripheral situations of a host vehicle, such that the driver of the host vehicle can recognize the peripheral situations.

CITED REFERENCES

Patent Documents

Korean Patent Laid-Open Publication No. 2013-0023535 (2013 Mar. 8)
Korean Patent Laid-Open Publication No. 2014-0050424 (2014 Apr. 29)
Japanese Patent Laid-Open Publication No. 2015-0210734 (2015 Nov. 24)

SUMMARY

Therefore, it is an aspect of the present disclosure to provide a system and method for controlling a vehicle based on a driver status, analyze a driver status by monitoring the driver's face and pupils during vehicle driving, and control the vehicle to stop on a road shoulder when it seems that the driver has no intention to drive the vehicle, resulting in safe and more stable vehicle driving.

Additional aspects of the invention will be set forth in part in the description which follows and, in part, will be obvious from the description, or may be learned by practice of the invention.

In accordance with an aspect of the present disclosure, a system and method for controlling a vehicle based on a driver status are disclosed. The vehicle control system includes various sensing devices (including a camera, a vehicle dynamics sensor, a vehicle around view monitoring (AVM) camera, a periphery surveillance sensor, and a navigation device) and an electronic control unit (ECU). The ECU may analyze a driver status through the driver's face and pupils recognized by output signals of the sensing devices. If the driver has no intention to drive the vehicle, the ECU may control the vehicle to stop on a road shoulder.

If the analyzed driver status is considered normal, the ECU may analyze the driver's pupils, such that the ECU may also control the vehicle based on movement of the driver's pupils.

BRIEF DESCRIPTION OF THE DRAWINGS

These and/or other aspects of the invention will become apparent and more readily appreciated from the following description of the embodiments, taken in conjunction with the accompanying drawings of which:

FIG. 1 is a block diagram illustrating a system for controlling a vehicle according to an embodiment of the present disclosure.

FIG. 2 is a flowchart illustrating a method for controlling a vehicle according to an embodiment of the present disclosure.

FIG. 3 is a flowchart illustrating a method for directing a vehicle to move toward a road shoulder and controlling the vehicle to stop on the road shoulder according to an embodiment of the present disclosure.

FIG. 4 is a conceptual diagram illustrating a method for directing a vehicle to move toward a road shoulder according to an embodiment of the present disclosure.

FIG. 5 is a flowchart illustrating a method for analyzing the driver's pupils according to an embodiment of the present disclosure.

DETAILED DESCRIPTION

Advantages and features of the present disclosure and a method of achieving the advantages and features of the present disclosure will be clearly understood from embodiments described hereinafter in conjunction with the accompanying drawings. However, the present disclosure is not limited to the following embodiments and may be realized in various different forms. These embodiments are provided only to completely disclose the present disclosure and for a person having ordinary skill in the art to which the present disclosure pertains to completely understand the category of the disclosure. That is, the present disclosure is defined only by the claims. The same reference numbers will be used throughout this specification to refer to the same parts.

A system and method for controlling a vehicle based on a driver status according to an embodiment of the present disclosure will hereinafter be described with reference to the attached drawings.

FIG. 1 is a block diagram illustrating a system for controlling a vehicle according to an embodiment of the present disclosure.

Referring to FIG. 1, the system for controlling the vehicle according to the present disclosure may include a sensing device 10, an electronic control unit (ECU) 20, a driver carelessness warning device 30, an acceleration/deceleration control device 40, and a steering control device 50. The sensing device 10 may include a driver surveillance camera 11, a vehicle dynamics sensor 12, a vehicle around view monitoring (AVM) camera 13, a periphery surveillance sensor 14, and a navigation device 15.

The driver surveillance camera 11 may be any one of various well-known image sensors such as a Far Infrared Ray (FIR) camera, and may be provided in an indoor space of the vehicle. The driver surveillance camera 11 may acquire images of the driver's face and pupils, and may thus transmit driver monitoring information (for example, a change in the driver's facial expression, eye blinking of the driver, movement of the driver's pupils, the driver's gaze position, etc.) to the ECU 20.

The vehicle dynamics sensor 12 may be implemented as any of various well-known sensors, for example, a wheel speed sensor, an acceleration sensor, a yaw rate sensor, a steering angle sensor, etc. The vehicle dynamics sensor 12 may be arranged at proper positions of a host vehicle, for example, a wheel, a steering wheel, or the like, such that the vehicle dynamics sensor 12 may sense a driving speed, acceleration, yaw angular speed, information as to whether the driver grasps a steering angle, etc. of the host vehicle, and may transmit the recognized information to the ECU 20.

The vehicle AVM camera 13 may be implemented as any of various well-known image sensors, for example, an FIR camera, a CMOS camera (or a CCD camera), etc. The vehicle AVM camera 13 may be arranged at an upper end of a windshield of a host vehicle, may sense and project various kinds of lights, for example, infrared light, visible light, etc., within the range of a predefined angle and a predefined distance with respect to a forward region of the host vehicle, may acquire an image of an external object located ahead of the host vehicle, an image of a vehicle lane, an image of a traffic sign, etc., and may transmit the recognized vehicle omnidirectional information to the ECU 20.

The periphery surveillance sensor 14 may be implemented as any of various well-known sensors, such as a radar sensor, etc. The periphery surveillance sensor 14 may be implemented as a plurality of periphery surveillance sensors 14. The peripheral surveillance sensors 14 may be respectively installed at a center part of a front surface, a center part of a rear surface, and a corner part of the host vehicle, may emit electromagnetic waves within the range of a predetermined angle with respect to a forward region of each periphery surveillance sensor, may receive electromagnetic waves reflected from peripheral objects located in the vicinity of the host vehicle, and may detect an angle, a distance, a relative speed, a relative acceleration, etc. between the host vehicle and each peripheral object, such that the peripheral surveillance sensors 14 may transmit the recognized vehicle peripheral information to the ECU 20.

The navigation device 15 may confirm a current position of the host vehicle through a Global Positioning System (GPS), may display a map to a destination, may confirm a distance to the destination and a total consumption time to be consumed to arrive at the destination, and may display a route to the destination for driver convenience, such that the navigation device 15 may allow the driver to easily drive the host vehicle. In addition, when a roadside assistance service is needed due to occurrence of an emergency situation or a faulty operation of the vehicle running on a road or when an emergency rescue service is needed due to occurrence of a traffic accident, the navigation device 15 may be a machine or program capable of informing the vehicle of a current GPS position. The navigation device 15 may transmit information about a current road and lane on which the host vehicle is running, information about a shoulder of the road, etc. to the ECU 20.

The ECU 20 may recognize the driver's face and pupils upon receiving signals detected by the sensing device 10, may analyze a driver status through the recognized driver's face and pupils, and may determine whether the driver has an intention to continuously drive the host vehicle. If it is determined that the driver has no intention to continuously drive the host vehicle, the ECU 20 may control the host vehicle to stop on a road shoulder, resulting in guarantee of safer driving.

If the analyzed driver status is considered normal, the ECU 20 may analyze movement of the driver's pupils, such that the ECU 20 may also control the vehicle based on the movement of the driver's pupils.

The driver carelessness warning device 30 may warn the driver of a careless driving status upon receiving a control signal from the ECU 20. Upon receiving a control signal from the ECU 20, the acceleration/deceleration control device 30 may increase engine power of the host vehicle or may generate a braking pressure of the host vehicle. The steering control device 50 may generate a steering angle of the steering wheel upon receiving a control signal from the ECU 20.

The present disclosure may analyze a driver status through the driver's face and pupils. If it seems that the driver has no intention to drive the vehicle, the present disclosure may control the vehicle to stop on a road shoulder, resulting in guarantee of safe driving.

In addition, if it seems that the driver status can be considered normal, the present disclosure may analyze movement of the driver's pupils, such that the vehicle can be controlled based on such movement of the driver's pupils. A detailed description thereof will hereinafter be given with reference to the attached drawings.

A method for controlling a vehicle based on a driver status using the above-mentioned system according to the embodiment of the present disclosure will hereinafter be described with reference to FIGS. 2 to 4.

FIG. 2 is a flowchart illustrating a method for controlling the vehicle using the vehicle control system according to an embodiment of the present disclosure.

Referring to FIG. 2, the system for controlling the vehicle based on a driver status according to the present disclosure may acquire images about the driver's face and pupils through the driver surveillance camera 11, such that the system may recognize driver monitoring information (e.g., a change in the driver's facial expression, eye blinking of the driver, movement of the driver's pupils, the driver's gaze position, etc.) through the acquired images (S210).

The system may analyze a driver status using the recognized driver monitoring information (S220). For example, if the driver's face is wrinkled or distorted, the system may determine that there is something wrong with the driver's health. In addition, the system may recognize occurrence or non-occurrence of drowsy driving by analyzing movement of the driver's pupils, the number of eye blinking times of the driver's eyes, and a closed or open state of the driver's eyes. In more detail, if the driver's pupils frequently and repeatedly move in up, down, right and left directions, this means that the driver feels sleepy. If the driver's eyes blink slowly, this means that the driver is in a drowsy driving status. In addition, if it seems that the driver's eyes are closed for a little while, this means that the driver fell asleep. In addition, for example, if the vehicle frequently deviates from a current lane, if the driver does not grasp the steering wheel, and if a change in distance between the vehicle and a peripheral vehicle suddenly increases, this means that the driver feels sleepy or fell asleep.

If the analyzed driver status is considered abnormal (S220), the system may warn the driver of drowsy or careless driving through the driver carelessness warning device 30 (S232). In this case, the driver carelessness warning device 30 may receive a control signal from the ECU 20, such that the driver carelessness warning device 30 may sequentially perform a first warning action based on visual sensation→a second warning action based on audio-visual sensation→a third warning action based on audio-visual sensation and tactile sensation (e.g., steering wheel vibration) according to lapse of time.

If it is determined that the driver has no intention to drive the vehicle irrespective of the warning actions shown in step S232 (e.g., if the driver's eyes do not move for a predetermined time, or if the driver does not move the steering wheel or does not depress an accelerator or brake pedal for a predetermined time), the system may recognize rear-view and side-view regions of the host vehicle and information about peripheral objects of the host vehicle through the vehicle dynamics sensor 12, the vehicle AVM camera 13, the periphery surveillance sensor 14, and the navigation device 15, may analyze a forward driving route of the host vehicle, and may determine whether the host vehicle can move toward a road shoulder on the basis of the analyzed result. If it is determined that the host vehicle can move toward the road shoulder, the system may guide the host vehicle to move toward the road shoulder and may control the host vehicle to stop on the road shoulder. On the other hand, if it is determined that the host vehicle is unable to move toward the road shoulder, the system may determine whether there is a high possibility of rear-end collision. If there is a high possibility of rear-end collision, the system may decelerate the vehicle or may control the vehicle to stop driving (S234). A method for guiding the host vehicle to move toward the shoulder and controlling the host vehicle to stop on the shoulder will hereinafter be described with reference to FIGS. 3 and 4.

If the analyzed driver status is considered normal (S220), the system may analyze the driver's pupils (S242), such that the system may control the vehicle based on movement of the driver's pupils (S244). A method for analyzing movement of the driver's pupils will hereinafter be described with reference to FIG. 5.

FIG. 3 is a flowchart illustrating a method for directing a vehicle to move toward a road shoulder and controlling the vehicle to stop on the road shoulder according to an embodiment of the present disclosure. FIG. 4 is a conceptual diagram illustrating a method for directing a vehicle to move toward a road shoulder according to an embodiment of the present disclosure.

Referring to FIG. 3, if it is determined that the driver has no intention to drive the vehicle irrespective of the warning actions shown, the system may detect the presence or absence of a shoulder on a current road (S310). In more detail, if the system receives information about the presence of a shoulder in a forward region of the host vehicle, information about horizontal/vertical distances from the host vehicle to a start point of the shoulder, and information about horizontal/vertical distances from the host vehicle to the end point of the shoulder from the navigation device 15, or if the system recognizes the presence of a right solid lane and a road edge of a next lane using the vehicle AVM camera 13, the system may determine the presence of the shoulder.

Subsequently, the system may recognize a current position of the host vehicle (S320). The system may determine whether a current position of the host vehicle is in the lane next to the shoulder (i.e., the lane nearest to the shoulder) upon receiving the horizontal distance from the host vehicle to the start point of the shoulder from the navigation device 15. If the horizontal distance from the host vehicle to the start point of the shoulder is equal to or shorter than a predetermined distance, the system may determine that the host vehicle is located in the lane next to the shoulder. Alternatively, if the presence of a road edge of the next lane is decided by information acquired by the vehicle AVM camera 13, the system may determine that the host vehicle is traveling in the lane nearest to the shoulder.

If it is determined that the host vehicle does not travel in the lane nearest to the shoulder (S320), the system may recognize the presence or absence of objects located in backward and peripheral regions of the host vehicle using the vehicle dynamics sensor 12, the vehicle AVM camera 13, and the periphery surveillance sensor 14, and may determine whether the host vehicle can perform lane change based on the recognized result. If it is determined that the host vehicle can perform lane change, the system may control the host vehicle to move into the next lane (S322).

If the host vehicle travels in the lane nearest to the shoulder (S320 or S322), the system may calculate a width of a shoulder lane, and may determine whether the shoulder lane has a sufficiently large width (e.g., a minimum width of 2.8 meters) in which the host vehicle can stop (S330).

If it is determined that the shoulder lane width is equal to or longer than 2.8 meters (S330), the system may detect the presence or absence of another vehicle traveling on the shoulder using the vehicle dynamics sensor 12, the vehicle AVM camera 13, and the periphery surveillance sensor 14 (S340).

Upon receiving information about the distance from the host vehicle to the end point of the shoulder from the navigation device 15 (S340) or upon receiving the end point of a road edge recognized by the vehicle AVM camera 13 (S340), the system may calculate a vehicle stop point where the host vehicle will stop driving using the received information (S350). Finally, the system may control the host vehicle to move toward the stop point calculated in step S350, and may control the host vehicle to stop at the calculated stop point (S360).

After completion of step S360, the system may turn on an emergency light, or may transmit vehicle information, driver information, and driver status information of the host vehicle to a central control center, such that the driver of the host vehicle may request an ambulance or police from the central control center. In this case, the system may confirm the driver's health information in advance. If the system determines that the driver has any health problem on the basis of health history information, the system may request an ambulance from the central control center. If the system determines that the driver does not awake after lapse of a predetermined time, the system may request the police from the central control center.

FIG. 5 is a flowchart illustrating a method for analyzing the driver's pupils according to an embodiment of the present disclosure.

Referring to FIG. 5, if the analyzed driver status is considered normal, the system may first perform zero calibration once on the image of the driver's pupils (S510). In this case, when the driver gazes at a left lane with respect to a current lane, position information of the driver's pupils captured by the camera may be stored. When the driver looks forward in the current lane, position information of the driver's pupils captured by the camera may be stored. In addition, when the driver gazes at a right lane with respect to the current lane, position information of the driver's pupils captured by the camera may be stored.

Thereafter, meaningless movement irrelevant to vehicle control from among various movements of the driver's pupils may be filtered out (S520). Current gaze position information of the driver may be transmitted to the vehicle AVM camera 13 (S522), and the vehicle AVM camera 13 may detect the presence or absence of any object within regions gazed at by the driver (S524). If the detected object is not identical to a vehicle lane or a road, the system may determine that movement of the driver's pupils is meaningless movement irrelevant to vehicle control (S526).

Finally, the system may detect the presence or absence of meaningful movement of the driver's pupils requesting vehicle control (S530). In more detail, if movement of the driver's pupils is not identical to meaningless movement irrelevant to vehicle control (S520), if a vehicle lane is detected in the regions gazed at by the driver, and if the driver gazes at a vehicle lane region in which the host vehicle is scheduled to enter, for a predefined time, the system may determine occurrence of movement of the driver's pupils requesting vehicle control, such that the vehicle may control the host vehicle to perform lane change. Alternatively, if the system determines that the driver was surprised while driving on the basis of movement of the driver's pupils (e.g., dilation of the driver's pupils), the system may perform vehicle braking control.

As is apparent from the above description, a system and method for controlling a vehicle based on a driver status according to the embodiments of the present disclosure can analyze a driver status by monitoring the driver's face and pupils during vehicle driving, and can control the vehicle to stop on a road shoulder when it seems that the driver has no intention to drive the vehicle, resulting in safer and more stable vehicle driving.

If the analyzed driver status is considered normal, the system and method for controlling the vehicle may monitor the driver's pupils, and may control the vehicle based on movement of the driver's pupils as necessary.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. A method for controlling a vehicle comprising:
acquiring, by a driver surveillance camera, images of a driver's face and a movement of the driver's pupils;
receiving, by a controller, the acquired images as driver monitoring information;
analyzing, by the controller, a driver status using the images of the driver's face and the movement of the driver's pupils;
determining whether the analyzed driver status is normal or abnormal;
upon determining that the analyzed driver status is abnormal, controlling, by the controller, the vehicle to move toward a road shoulder,
wherein the controlling the vehicle to move toward the road shoulder includes:
upon determining that the driver status is abnormal, warning the driver of careless driving before moving to the road shoulder,
upon determination that the driver has no intention to drive the vehicle irrespective of the warning of careless driving, determining whether the vehicle is able to move toward the road shoulder,
controlling the vehicle to move toward the road shoulder when the vehicle is able to move toward the road shoulder including, upon determining that a current position of the vehicle is not in a lane nearest to the road shoulder, controlling the vehicle to move from a current lane to the lane nearest to the road shoulder, and
controlling deceleration of the vehicle when the vehicle is unable to move toward the road shoulder; and
upon determining that the analyzed driver status is normal, analyzing the movement of the driver's pupils; and
controlling, by the controller, vehicle movement based on the movement of the driver's pupils,
wherein the analyzing of the movement of the driver's pupils comprises filtering out meaningless movement irrelevant to vehicle control from among movements of the driver's pupil, and
the filtering out meaningless movement of the driver's pupils comprises:
obtaining current gaze position information of the driver acquired by the driver surveillance camera;
detecting a presence of any object within regions gazed at by the driver using information acquired by a vehicle around view monitoring (AVM) camera based on the current gaze position information; and
upon determining that the detected object is not a vehicle lane or road, determining the movement of the driver's pupils to be the meaningless movement.

2. The method according to claim 1, wherein the controlling the vehicle to move toward the road shoulder further includes:
detecting a presence or absence of the road shoulder in which the vehicle is able to enter;
determining whether the current position of the vehicle is in the lane nearest to the detected road shoulder;
determining whether the road shoulder has a sufficiently large width in which the vehicle is able to stop on the road shoulder;
detecting a presence or absence of any other vehicle traveling on the road shoulder;

upon determining that the any other vehicle traveling on the road shoulder is not detected, calculating a vehicle stop point on the road shoulder; and controlling the vehicle to move toward to stop at the calculated stop point of the road shoulder.

3. The method according to claim 2, wherein the detecting a presence or absence of the road shoulder in which the vehicle is able to enter includes:

upon receiving, from a navigation device, at least one of information about the presence of the road shoulder in a forward region of the vehicle, information about horizontal and vertical distances from the vehicle to a start point of the road shoulder, or information about horizontal and vertical distances from the vehicle to an end point of the road shoulder, detecting the road shoulder based on the received information; or if a solid line and a road edge at a right side of the vehicle are recognized through the vehicle around view monitoring (AVM) camera, detecting the road shoulder based on the recognized information.

4. The method according to claim 2, wherein the determining whether the current position of the vehicle is in the lane nearest to the road shoulder includes:

receiving a horizontal distance from the vehicle to a start point of the road shoulder from a navigation device; and if the received horizontal distance from the vehicle to the start point of the road shoulder is equal to or shorter than a predetermined distance, determining that the current position of the vehicle is in the lane nearest to the road shoulder.

5. The method according to claim 2, wherein the calculating the vehicle stop point on the road shoulder includes calculating the vehicle stop point on the shoulder using a distance from the vehicle to an end point of the shoulder or using an end point of a road edge.

6. The method according to claim 1, wherein the controlling the vehicle to move from the current lane to the lane nearest to the road shoulder includes:

recognizing information about objects located in backward and surrounding regions of the vehicle through a vehicle dynamics sensor, the vehicle around view monitoring (AVM) camera, and a periphery surveillance sensor, and determining whether lane change of the vehicle is available based on the recognized information; and upon determining that the lane change of the vehicle is available, controlling the vehicle to move from the current lane to the lane nearest to the road shoulder.

7. The method according to claim 1, further comprising at least one of:

turning on an emergency light; or transmitting vehicle information, driver information, and driver status information to a central control center.

8. The method according to claim 1, wherein the analyzing of the movement of the driver's pupils further comprises:

performing calibration on an image of the driver's pupils; and detecting movement of the driver's pupils requesting control of vehicle movement from among the movements of the driver's pupils.

9. The method according to claim 8, wherein the performing calibration on an image of the driver's pupils includes:

when the driver gazes at a left lane with respect to the current lane, storing position information of the driver's pupils captured by the driver surveillance camera;

when the driver looks forward in the current lane, storing position information of the driver's pupils captured by the driver surveillance camera; and when the driver gazes at a right lane with respect to the current lane, storing position information of the driver's pupils captured by the driver surveillance camera.

10. The method according to claim 8, wherein the detecting movement of the driver's pupils requesting control of the vehicle movement includes, upon determining that the movement of the driver's pupils is not identical to the meaningless movement, a vehicle lane is detected in regions gazed at by the driver, and the driver gazes at a vehicle lane region, in which the vehicle is entering, for a predetermined period of time, determining occurrence of the movement of the driver's pupils requesting control of vehicle movement.

11. The method according to claim 8, wherein the detecting movement of the driver's pupils requesting control of vehicle movement includes, if dilation of the driver's pupils occurs, determining the occurrence of movement of the driver's pupils requesting control of vehicle movement.

* * * * *